United States Patent [19]

Geiss et al.

[11] Patent Number: 4,710,496

[45] Date of Patent: Dec. 1, 1987

[54] PYRROL-1-YLPHENYLDIHY-DROPYRIDAZINONES, THEIR PREPARATION AND THEIR USE

[75] Inventors: Karl-Heinz Geiss, Beindersheim; Bernhard Schmied, Dossenheim; Manfred Raschack, Weisenheim am Sand; Hans-Dieter Lehmann, Hirschberg; Josef Gries, Wachenheim; Klaus Ruebsamen, Neustadt, all of Fed. Rep. of Germany

[73] Assignee: BASF Aktiengesellschaft, Fed. Rep. of Germany

[21] Appl. No.: 753,278

[22] Filed: Jul. 9, 1985

[30] Foreign Application Priority Data

Jul. 12, 1984 [DE] Fed. Rep. of Germany ....... 3425632

[51] Int. Cl.$^4$ .................... A61K 31/50; C07D 403/10; C07D 403/14; C07D 401/14
[52] U.S. Cl. .................................. 514/183; 514/212; 514/248; 514/252; 544/235; 544/238; 544/234; 540/481; 540/598; 540/599
[58] Field of Search ................ 544/238, 235; 514/252, 514/248, 183, 212; 260/243.3; 540/481, 598, 599

[56] References Cited

FOREIGN PATENT DOCUMENTS 0075436 9/1982 European Pat. Off. .

OTHER PUBLICATIONS

W. Curran et al., "6-Phenyl-4,5-dihydro-3(2-H)-pyridazinones. A Series of Hypotensive Agents", *Journal of Medicinal Chemistry*, pp. 273-281 (1974), vol. 17.

E. Steck et al., "Pyridazines, VI, Some 6-Substituted 3(2H) pyridazinones (1)", *Journal of Medicinal Chemistry*, pp. 755-761, vol. 11 (1974).

M. Thyes et al., "6-Aryl-4,5-dihydro-3(2H)-pyridazinones. A new Class of Compounds with Platelet Aggregation Inhibiting and Hypotensive Activities", *Journal of Medicinal Chemistry*, pp. 800-807, vol. 26 (1983).

*Primary Examiner*—Mark L. Berch
*Attorney, Agent, or Firm*—Keil & Weinkauf

[57] ABSTRACT

Novel pyrrol-1-ylphenyldihydropyridazinones of the formula

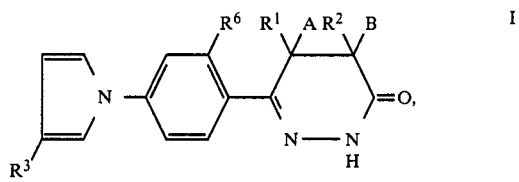

their preparation and their use in the treatment of disorders.

13 Claims, No Drawings

PYRROL-1-YLPHENYLDIHYDROPYRIDAZINONES, THEIR PREPARATION AND THEIR USE

The present invention relates to novel pyrrol-1-yl-phenyldihydropyridazinones, a process for their preparation, and their use for treating disorders.

6-Aryldihydropyridazinones which have pharmacological effects have been disclosed (cf. J. Med. Chem. 17 (1974), 273, J. Het. Chem. 11 (1974), 755 and J. Med. Chem. 26 (1983), 800). A number of 6-phenyldihydropyridazinones which increase myocardial contractility and have an antihypertensive action are described in European Laid-Open Application 75,436.

We have found that pyrrol-1-ylphenyldihydropyridazinones of the formula I

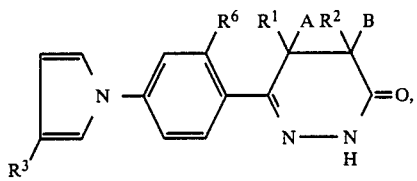

where $R^1$ is hydrogen, methyl or hydroxymethyl, $R^2$ is hydrogen or methyl, or $R^1$ and $R^2$ together form a methylene or ethylene radical, A and B are each hydrogen or, where $R^1$ and $R^2$ do not form an alkylene group, they furthermore may be a common bond, $R^3$ is formyl or hydroxymethyl or $CH_2$—$NR^4R^5$ where $R^4$ is $C_1$-$C_6$-alkyl or phenyl-$C_1$-$C_3$-alkylene and $R^5$ is hydrogen, $C_1$-$C_6$-alkyl or formyl or $R^4$ and $R^5$ together form a $C_4$-$C_7$-alkylene radical, and $R^6$ is hydrogen or, together with $R^1$, forms a radical —$(CH_2)_m$—, where m is 0, 1, 2 or 3, and, if appropriate, their addition salts with acids possess useful pharmacological properties.

The compounds of the formula I in which $R^3$ is $CH_2$—$NR^4R^5$ and $R^5$ is not formyl can form salts with acids, suitable acids being those which are physiologically tolerated. These include, in particular, sulfuric acid, phosphoric acid, amidosulfonic acid, nitric acid and organic acids, such as acetic acid, propionic acid, oxalic acid, malonic acid, succinic acid, fumaric acid, maleic acid, citric acid, tartaric acid or lactic acid.

$R^1$ is preferably hydrogen or methyl, in particular the latter, $R^2$ is preferably hydrogen, and $R^1$ and $R^2$ preferably form a methylene or ethylene radical, in particular the former, A and B are each preferably hydrogen and $R^6$ is preferably hydrogen or, together with $R^1$, forms a radical —$(CH_2)_m$— where m is 1 or 2; in particular $R^6$ is hydrogen.

The novel compounds are prepared by a process in which a p-aminophenyldihydropyridacinone of the formula II

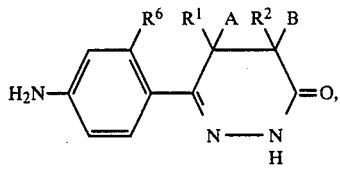

where $R^1$, $R^2$, $R^6$, A and B have the above meanings, is reacted with a tetrahydrofuran of the formula III

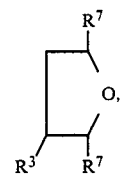

where $R^3$ has the stated meanings and $R^7$ is $C_1$-$C_4$-alkoxy, $C_1$-$C_4$-acyloxy, chlorine or bromine, and, if required, the compound thus obtained is reduced to the compound I in which $R^3$ is $CH_2OH$ if $R^3$ is formyl, or is converted by reductive amination to the amine I in which $R^3$ is $CH_2NR^4R^5$.

$R^7$ is preferably $C_1$-$C_4$-alkoxy, in particular methoxy.

The novel compounds are prepared either in a lower alkanecarboxylic acid, such as acetic acid, or in an organic solvent with the addition of an acidic catalyst, such as an inorganic acid, an organic carboxylic acid or a sulfonic acid. They may also be prepared in presence of an acidic ion exchanger. The catalyst is used in an amount of from 0.01 to 300 mol %, from 0.01 to 20, preferably from 0.1 to 10, mol % being used for the preparation of the compounds I in which $R^3$ is hydroxymethyl, formyl or $CH_2$—$NR^4R^5$, where $R^5$ is formyl, and from 100 to 300, preferably from 100 to 150, mol % being employed for the preparation of the compounds I in which $R^3$ is $CH_2$—$NR^4R^5$, where $R^5$ is not formyl. The reaction can be carried out under atmospheric or superatmospheric pressure and from room temperature to the reflux temperature of the solvent used. Usually, the temperatures employed are from 20° to 160° C., preferably from 60° to 120° C. Suitable organic solvents are aromatic hydrocarbons, such as benzene, toluene, ethylbenzene, dichlorobenzene, o-, m- or p-xylene or methylnaphthalene, aliphatic and cycloaliphatic hydrocarbons, such as naphtha, heptane or cyclohexane, ethers, such as diethyl ether or tetrahydrofuran, amides, such as N,N-dimethylformamide or N,N-dimethylacetamide and N-methylpyrrolidone, as well as mixtures of these solvents.

The compounds I in which $R^3$ is CHO are preferably prepared in a lower alkanecarboxylic acid, in particular acetic acid, at from 60° to 120° C., in particular from 70° to 100° C.

The amines I in which $R^3$ is $CH_2NR^4R^5$, where $R^5$ is $C_1$-$C_6$-alkyl, are preferably prepared in aromatic hydrocarbons as solvents, in particular toluene, in the presence of from 100 to 150 mol % of an organic sulfonic acid, in particular toluenesulfonic acid, at from 90° C. to the reflux temperature, in particular at the reflux temperature of the solvent used.

The amines of the formula I in which $R^3$ is $CH_2$—$NR^4R^5$, where $R^5$ is hydrogen or formyl, are preferably prepared by reacting a compound of the formula III, where $R^3$ is

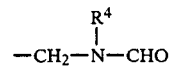

in a solvent such as a lower alkanecarboxylic acid, in particular acetic acid, at from 70° to 100° C., or in an aromatic hydrocarbon, such as toluene, in the presence of from 0.1 to 10 mol % of an organic sulfonic acid, such as toluenesulfonic acid, at from 90° C. to the reflux temperature. If desired, the formyl group can subsequently be eliminated by alkaline hydrolysis with NaOH.

The compounds of the formula I in which $R^3$ is $-CH_2-NR^4R^5$, where $R^5$ is not formyl, can be obtained by reductive amination of a compound of the formula I, where $R^3$ is formyl, with an amine of the formula $R^4R^5NH$, in which $R^5$ is not formyl. The reductive amination can be effected in a suitable solvent, for example using a platinum, palladium, nickel or cobalt catalyst and hydrogen or with the aid of an organometallic hydride, such as sodium borohydride or sodium cyanoborohydride, or by the Leuckhart-Wallach method using formic acid. Compounds of the formula I in which $R^3$ is $CH_2NHR^4$ can then be formylated to the compounds I in which $R^3$ is

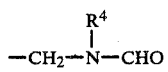

Compounds of the formula I in which $R^3$ is hydroxymethyl can be prepared by reducing the corresponding formyl compound. This reduction can be carried out, for example, with hydrogen and a platinum, palladium, nickel or cobalt catalyst, or with an organometallic hydride, such as sodium borohydride or lithium aluminum hydride.

The compounds according to the invention are useful for inhibiting platelet aggregation and possess valuable cardiotonic properties. They also reduce blood pressure and inhibit secretion of gastric acid, in which respect they are substantially superior to the comparative compound p-(pyrrol-1-yl)-phenyl-4,5-dihydropyridazin-3-one (European Pat. No. 75,436).

The novel compounds can be administered orally or parenterally (subcutaneously, intravenously, intramuscularly or intraperitoneally) in a conventional manner.

The dosage depends on the age, condition and weight of the patient and on the route of administration. As a rule, the daily dose of active compound per patient is from about 0.1 to 10, preferably from 0.5 to 5, mg in the case of parenteral administration and from 1 to 100, preferably from 5 to 50, mg in the case of oral administration.

The novel compounds may be employed in the conventional solid or liquid pharmaceutical forms, for example tablets, film tablets, capsules, powders, granules, coated tablets, solutions or suppositories. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or antioxidants (cf. H. Sucker et al: Pharmazeutische Technologie, Thieme-Verlag, Stuttgart 1978). The formulations thus obtained normally contain from 0.1 to 99% by weight of the active compound.

The Examples which follow illustrate the invention.

EXAMPLE 1A

A solution of 33.6 g (210 millimoles) of 2,5-dimethoxytetrahydrofuran-3-carbaldehyde in 200 ml of glacial acetic acid was added dropwise to 40.6 g (200 millimoles) of 6-(4-aminophenyl)-4,5-dihydro-5-methylpyridazinone in 400 ml of glacial acetic acid at 80° C. After 2 hours, the reaction mixture was poured into saturated $NaHCO_3$ solution and extracted with $CH_2Cl_2$. The extract was washed with water and saturated NaCl solution and dried over $Na_2SO_4$, the solvent was stripped off in a rotary evaporator, and the residue was then recrystallized from dimethylformamide (DMF)/water. 44.2 g of 6-[p-(3-formylpyrrol-1-yl)-phenyl]-4,5-dihydro-5-methylpyridazinone of melting point 191°–192° C. were obtained.

The compounds of the formula I, where $R^3$ is CHO, were obtained, or can be prepared, in a similar manner by reacting the corresponding 6-(4-aminophenyl)-pyridazinones with 2,5-dimethoxytetrahydrofuran-3-carbaldehyde:

| Example | $R^6$ | $R^1$ | $R^2$ | A | B | Mp. [°C.] |
|---|---|---|---|---|---|---|
| 1B | H | H | H | H | H | 192–194(a) |
| 1C | H | $-(CH_2)-$ | | H | H | 241–242 |
| 1D | H | $-(CH_2)_2-$ | | H | H | 186–188 |
| 1E | H | H | $CH_3$ | H | H | 192–194 |
| 1F | H | H | H | common bond | | 256–258(a) |
| 1G | H | H | $CH_3$ | common bond | | 228–230(b) |
| 1H | H | $CH_3$ | H | common bond | | >260 |
| 1I | H | $CH_2OH$ | H | H | H | |
| 1K | common bond | | H | H | H | |
| 1L | $-CH_2-$ | | H | H | H | |
| 1M | $-(CH_2)_2-$ | | H | H | H | 225–227(c) |
| 1N | $-(CH_2)_3-$ | | H | H | H | |

(a)The polymeric residue formed in the reaction was boiled thoroughly with acetone, and the residual acetone phase was combined with the extract of the aqueous solution.
(b)Recrystallization from methanol.
(c)Recrystallization from acetone/petroleum ether.

EXAMPLE 2A 4.2 g (15 millimoles) of 6-[p-(3-formylpyrrol-1-yl)-phenyl]-5, 6-dihydro-5-methylpyridazin-3-one (Example 1A) were dissolved in 50 ml of ethanol and 20 ml of dimethylformamide (DMF), and 1.15 g (30 millimoles) of sodium borohydride were added. The mixture was stirred for 6 hours at 60° C. (conversion monitored by thin layer chromatography using $SiO_2$ and 9:1 $CH_2Cl_2/CH_3OH$), after which 50 ml of water were added, the mixture was extracted with ethyl acetate, the ethyl acetate phase was dried and the solvent was stripped off in a rotary evaporator to give a yellow crystalline solid. Recrystallization from DMF/$H_2O$ gave 2.5 g of 6-[p-(3-hydroxymethyl-pyrrol-1-yl)-phenyl]-4, 5-dihydro-5-methylpyridazinone of melting point 184°–186° C.

The compounds of Examples 2B to 2N (I, $R^3=CH_2OH$) were obtained, or can be prepared, by a similar procedure, by reacting the compounds of Examples 1B to 1N with sodium borohydride:

| Example | $R^6$ | $R^1$ | $R^2$ | A | B | Mp. [°C.] |
|---|---|---|---|---|---|---|
| 2B | H | H | H | H | H | >260(a) |
| 2C | H | $-(CH_2)-$ | | H | H | 214–216(b) |
| 2D | H | $-(CH_2)_2-$ | | H | H | amorphous |
| 2E | H | H | $CH_3$ | H | H | 198–200(c) |
| 2F | H | H | H | common bond | | 243–244 |
| 2G | H | H | $CH_3$ | common bond | | 253–255 |
| 2H | H | $CH_3$ | H | common bond | | from 225 (decomposition)(c) |
| 2I | H | $CH_2OH$ | H | H | H | |
| 2K | common bond | | H | H | H | |
| 2L | $-CH_2-$ | | H | H | H | |
| 2M | $-(CH_2)_2-$ | | H | H | H | 223–224 |

| Example | $R^6$ | $R^1$ | $R^2$ | A | B | Mp. [°C.] |
|---|---|---|---|---|---|---|
| 2N | —(CH$_2$)$_3$— | | H | H | H | |

(a)When the reaction mixture was diluted with water, the substance was precipitated in pure form.
(b)Recrystallization from DMF/H$_2$O was followed by recrystallization from methanol.
(c)Recrystallization from methanol.

EXAMPLE 3A 4.2 g (15 millimoles) of 6-[p-(3-formylpyrrol-1-yl)-phenyl]4, 5-dihydro-5-methylpyridazin-3-one (compound from Example 1A) in 30 ml of methanol were stirred with 3.36 g (30 millimoles) of 40% strength aqueous dimethylamine solution, 1.8 g (30 millimoles) of acetic acid and 0.75 g (12 millimoles) of sodium cyanoborohydride for 5 hours at room temperature (conversion monitored by thin layer chromatography using SiO$_2$ and 5:2:2 ethyl acetate/acetic acid/water). 50 ml of H$_2$O were added, the mixture was rendered alkaline with 2N NaOH and extracted with ethyl acetate, the organic phase was washed with water, dried with Na$_2$SO$_4$ and purified over a silica gel column using a 4:1 methylene chloride/methanol mixture, and the crystalline residue from the product-containing fractions was recrystallized from ethyl acetate/petroleum ether. 1.4 g of 6-[p-(3-dimethylaminomethylpyrrol-1-yl)-phenyl]-4, 5-dihydro-5-methylpyridazin-3-one of melting point 167°–168° C. were obtained.

The compounds of Examples 3B to 3M were obtained similarly to Example 3A, by reacting the compound of Example 1A with an amine R$^4$R$^5$NH.

| I, $R^1$ = CH$_3$, $R^2$ = $R^6$ = A = B = H, $R^3$ = —CH$_2$—NR$^4$R$^5$ ||||
|---|---|---|---|
| Example | $R^4$ | $R^5$ | Mp. [°C.] |
| 3B | —(CH$_2$)$_5$— | | 76–77 |
| 3C | C$_6$H$_5$CH$_2$ | CH$_3$ | 237–238 |
| 3D | n-C$_4$H$_9$ | n-C$_4$H$_9$ | 88–90(a) |
| 3E | i-C$_3$H$_7$ | H | 92–94 |
| 3F | n-C$_6$H$_{13}$ | H | from 105 (decomposition)(a) |
| 3G | C$_6$H$_5$—CH$_2$— | H | 135–137(b) |
| 3H | C$_6$H$_5$—CH(CH$_3$)— | H | from 125 (decomposition)(a) |
| 3I | —(CH$_2$)$_4$— | | 92–93(a) |
| 3K | —(CH$_2$)$_6$— | | 98–100(a) |
| 3L | —(CH$_2$)$_7$— | | 136–137(c) |
| 3M | CH$_3$ | H | 72–75(d) |

(a)After the extraction, one equivalent of tartaric acid was added to the crude product in methanol, the methanol was stripped off and the product was recrystallized from isopropanol.
(b)Recrystallization from DMF/ether and from isopropanol.
(c)Recrystallization from ethyl acetate.

EXAMPLES 4 TO 15

The following compounds of Examples 4 to 15 were obtained, or can be prepared, similarly to Example 3A, by reacting the compounds of Examples 1B–1N with an amine R$^4$R$^5$NH:

| I, $R^1$ = $R^2$ = $R^6$ = A = B = H, $R^3$ = CH$_2$NR$^4$R$^5$ ||||
|---|---|---|---|
| Example | $R^4$ | $R^5$ | Mp. [°C.] |
| 4A | CH$_3$ | CH$_3$ | amorphous(a) |
| 4B | —(CH$_2$)$_5$— | | |
| 4C | C$_6$H$_5$—CH$_2$ | CH$_3$ | |
| 4D | n-C$_4$H$_9$ | n-C$_4$H$_9$ | amorphous(a) |
| 4E | i-C$_3$H$_7$ | H | |
| 4F | n-C$_6$H$_{13}$ | H | |
| 4G | C$_6$H$_5$CH$_2$ | H | |
| 4H | C$_6$H$_5$(CH$_2$)$_3$— | H | |
| 4I | —(CH$_2$)$_4$— | | |
| 4K | —(CH$_2$)$_6$— | | |
| 4L | —(CH$_2$)$_7$— | | |
| 4M | CH$_3$ | H | |

(a)The substance was recrystallized from isopropanol, as the tartrate.

EXAMPLES 5A–5M

| I, $R^1$ + $R^2$ = —CH$_2$—, $R^6$ = A = B = H, $R^3$ = —CH$_2$NR$^4$R$^5$ ||||
|---|---|---|---|
| Example | $R^4$ | $R^5$ | Mp. [°C.] |
| 5A | CH$_3$ | CH$_3$ | |
| 5B | —(CH$_2$)$_5$— | | amorphous(a) |
| 5C | C$_6$H$_5$—CH$_2$ | CH$_3$ | |
| 5D | n-C$_4$H$_9$ | n-C$_4$H$_9$ | |
| 5E | i-C$_3$H$_7$ | H | |
| 5F | n-C$_6$H$_{13}$ | H | |
| 5G | C$_6$H$_5$CH$_2$ | H | |
| 5H | C$_6$H$_5$(CH$_2$)$_2$— | H | |
| 5I | —(CH$_2$)$_4$— | | |
| 5K | —(CH$_2$)$_6$— | | |
| 5L | —(CH$_2$)$_7$— | | |
| 5M | CH$_3$ | H | |

(a)The substance was recrystallized from isopropanol, as the tartrate.

EXAMPLES 6A–6M

| I, $R^1$ + $R^2$ = —(CH$_2$)$_2$—, $R^6$ = A = B = H, $R^3$ = —CH$_2$NR$^4$R$^5$ ||||
|---|---|---|---|
| Example | $R^4$ | $R^5$ | Mp. [°C.] |
| 6A | CH$_3$ | CH$_3$ | |
| 6B | —(CH$_2$)$_5$— | | |
| 6C | C$_6$H$_5$—CH$_2$ | CH$_3$ | amorphous(a) |
| 6D | n-C$_4$H$_9$ | n-C$_4$H$_9$ | |
| 6E | i-C$_3$H$_7$ | H | |
| 6F | n-C$_6$H$_{13}$ | H | |
| 6G | C$_6$H$_5$CH$_2$ | H | |
| 6H | C$_6$H$_5$(CH$_2$)$_2$— | H | |
| 6I | —(CH$_2$)$_4$— | | |
| 6K | —(CH$_2$)$_6$— | | |
| 6L | —(CH$_2$)$_7$— | | |
| 6M | CH$_3$ | H | |

The substance was recrystallized from isopropanol, as the tartrate.

EXAMPLES 7A TO 7M

| I, $R^1$ = H, $R^2$ = CH$_3$, $R^6$ = A = B = H, $R^3$ = —CH$_2$NR$^4$R$^5$ ||||
|---|---|---|---|
| | $R^4$ | $R^5$ | [°C.] |
| 7A | CH$_3$ | CH$_3$ | |
| 7B | —(CH$_2$)$_5$— | | |
| 7C | C$_6$H$_5$—CH$_2$ | CH$_3$ | |
| 7D | n-C$_4$H$_9$ | n-C$_4$H$_9$ | |
| 7E | i-C$_3$H$_7$ | H | 220–222(a) |
| 7F | n-C$_6$H$_{13}$ | H | |
| 7G | C$_6$H$_5$CH$_2$ | H | |
| 7H | C$_6$H$_5$(CH$_2$)$_2$— | H | |
| 7I | —(CH$_2$)$_4$— | | |
| 7K | —(CH$_2$)$_6$— | | |
| 7L | —(CH$_2$)$_7$— | | |
| 7M | CH$_3$ | H | |

(a)The semitartrate was recrystallized from isopropanol.

EXAMPLES 8A TO 8M

| | I, $R^1 = R^2 = R^6 = H$, A + B = common bond, $R^3 = -CH_2NR^4R^5$ | | |
|---|---|---|---|
| Example | $R^4$ | $R^5$ | Mp. [°C.] |
| 8A | $CH_3$ | $CH_3$ | |
| 8B | $-(CH_2)_5-$ | | 220-222(a) |
| 8C | $C_6H_5-CH_2$ | $CH_3$ | |
| 8D | $n-C_4H_9$ | $n-C_4H_9$ | |
| 8E | $i-C_3H_7$ | H | |
| 8F | $n-C_6H_{13}$ | H | |
| 8G | $C_6H_5CH_2$ | H | |
| 8H | $C_6H_5(CH_2)_2-$ | H | |
| 8I | $-(CH_2)_4-$ | | |
| 8K | $-(CH_2)_6-$ | | |
| 8L | $-(CH_2)_7-$ | | |
| 8M | $CH_3$ | H | |

(a) Recrystallization from methanol.

EXAMPLES 9A TO 9M

| | I, $R^1 = R^6 = H, R^2 = CH_3$, A + B = common bond, $R^3 = -CH_2NR^4R^5$ | | |
|---|---|---|---|
| Example | $R^4$ | $R^5$ | Mp. [°C.] |
| 9A | $CH_3$ | $CH_3$ | |
| 9B | $-(CH_2)_5-$ | | |
| 9C | $C_6H_5-CH_2$ | $CH_3$ | |
| 9D | $n-C_4H_9$ | $n-C_4H_9$ | |
| 9E | $i-C_3H_7$ | H | |
| 9F | $n-C_6H_{13}$ | H | amorphous(a) |
| 9G | $C_6H_5CH_2$ | H | |
| 9H | $C_6H_5(CH_2)_2-$ | H | |
| 9I | $-(CH_2)_4-$ | | |
| 9K | $-(CH_2)_6-$ | | |
| 9L | $-(CH_2)_7-$ | | |
| 9M | $CH_3$ | H | |

(a) Tartrate recrystallized from methanol/ether.

EXAMPLES 10A TO 10M

| | I, $R^1 = CH_3, R^2 = R^6 = H$, A + B = common bond, $R^3 = -CH_2NR^4R^5$ | | |
|---|---|---|---|
| Example | $R^4$ | $R^5$ | Mp. [°C.] |
| 10A | $CH_3$ | $CH_3$ | |
| 10B | $-(CH_2)_5-$ | | |
| 10C | $C_6H_5-CH_2$ | $CH_3$ | |
| 10D | $n-C_4H_9$ | $n-C_4H_9$ | |
| 10E | $i-C_3H_7$ | H | |
| 10F | $n-C_6H_{13}$ | H | |
| 10G | $C_6H_5CH_2$ | H | |
| 10H | $C_6H_5(CH_2)_2-$ | H | |
| 10I | $-(CH_2)_4-$ | | 183-185(a) |
| 10K | $-(CH_2)_6-$ | | |
| 10L | $-(CH_2)_7-$ | | |
| 10M | $CH_3$ | H | |

(a) Recrystallization from ethyl acetate.

EXAMPLES 11A TO 11M

| | I, $R^1 = CH_2OH, R^2 = R^6 = A = B = H, R^3 = CH_2NR^4R^5$ | |
|---|---|---|
| Example | $R^4$ | $R^5$ |
| 11A | $CH_3$ | $CH_3$ |
| 11B | $-(CH_2)_5-$ | |
| 11C | $C_6H_5-CH_2$ | $CH_3$ |
| 11D | $n-C_4H_9$ | $n-C_4H_9$ |
| 11E | $i-C_3H_7$ | H |
| 11F | $n-C_6H_{13}$ | H |
| 11G | $C_6H_5CH_2$ | H |
| 11H | $C_6H_5(CH_2)_2-$ | H |
| 11I | $-(CH_2)_4-$ | |
| 11K | $-(CH_2)_6-$ | |
| 11L | $-(CH_2)_7-$ | |
| 11M | $CH_3$ | H |

EXAMPLES 12A TO 12M

| | I, $R^1 + R^6$ = common bond, $R^2 = A = B = H, R^3 = CH_2NR^4R^5$ | |
|---|---|---|
| Example | $R^4$ | $R^5$ |
| 12A | $CH_3$ | $CH_3$ |
| 12B | $-(CH_2)_5-$ | |
| 12C | $C_6H_5-CH_2$ | $CH_3$ |
| 12D | $n-C_4H_9$ | $n-C_4H_9$ |
| 12E | $i-C_3H_7$ | H |
| 12F | $n-C_6H_{13}$ | H |
| 12G | $C_6H_5CH_2$ | H |
| 12H | $C_6H_5(CH_2)_2-$ | H |
| 12I | $-(CH_2)_4-$ | |
| 12K | $-(CH_2)_6-$ | |
| 12L | $-(CH_2)_7-$ | |
| 12M | $CH_3$ | H |

EXAMPLES 13A TO 13M

| | I, $R^1 + R^6 = -CH_2-, R^2 = A = B = H, R^3 = CH_2NR^4R^5$ | |
|---|---|---|
| Example | $R^4$ | $R^5$ |
| 13A | $CH_3$ | $CH_3$ |
| 13B | $-(CH_2)_5-$ | |
| 13C | $C_6H_5-CH_2$ | $CH_3$ |
| 13D | $n-C_4H_9$ | $n-C_4H_9$ |
| 13E | $i-C_3H_7$ | H |
| 13F | $n-C_6H_{13}$ | H |
| 13G | $C_6H_5CH_2$ | H |
| 13H | $C_6H_5(CH_2)_2-$ | H |
| 13I | $-(CH_2)_4-$ | |
| 13K | $-(CH_2)_6-$ | |
| 13L | $-(CH_2)_7-$ | |
| 13M | $CH_3$ | H |

EXAMPLES 14A TO 14M

| | I, $R^1 + R^6 = -CH_2CH_2-$, $R^2 = A = B = H, R^3 = CH_2NR^4R^5$ | |
|---|---|---|
| Example | $R^4$ | $R^5$ |
| 14A | $CH_3$ | $CH_3$ |
| 14B | $-(CH_2)_5-$ | |
| 14C | $C_6H_5-CH_2$ | $CH_3$ |
| 14D | $n-C_4H_9$ | $n-C_4H_9$ |
| 14E | $i-C_3H_7$ | H |
| 14F | $n-C_6H_{13}$ | H |
| 14G | $C_6H_5CH_2$ | H |
| 14H | $C_6H_5(CH_2)_2-$ | H |
| 14I | $-(CH_2)_4-$ | |
| 14K | $-(CH_2)_6-$ | |
| 14L | $-(CH_2)_7-$ | |
| 14M | $CH_3$ | H |

EXAMPLES 15A TO 15M

| | I, $R^1 + R^6 = -(CH_2)_3-$, $R^2 = A = B = H, R^3 = CH_2NR^4R^5$ | |
|---|---|---|
| Example | $R^4$ | $R^5$ |
| 15A | $CH_3$ | $CH_3$ |
| 15B | $-(CH_2)_5-$ | |
| 15C | $C_6H_5-CH_2$ | $CH_3$ |

| | I, $R^1 + R^6 =$ —(CH$_2$)$_3$—, $R^2 = A = B = H, R^3 = CH_2NR^4R^5$ | |
|---|---|---|
| Example | $R^4$ | $R^5$ |
| 15D | n-C$_4$H$_9$ | n-C$_4$H$_9$ |
| 15E | i-C$_3$H$_7$ | H |
| 15F | n-C$_6$H$_{13}$ | H |
| 15G | C$_6$H$_5$CH$_2$ | H |
| 15H | C$_6$H$_5$(CH$_2$)$_2$— | H |
| 15I | —(CH$_2$)$_4$— | |
| 15K | —(CH$_2$)$_6$— | |
| 15L | —(CH$_2$)$_7$— | |
| 15M | CH$_3$ | H |

EXAMPLE 16

1.0 g (5 millimoles) of 6-(4-aminophenyl)-4,5-dihydro-5-methyl-pyridazinone and 1.0 g (5 millimoles) of 2,5-dimethoxy-3-(N-formyl-N-methylaminomethyl)-tetrahydrofuran in 10 ml of acetic acid were stirred for 2 hours at 80° C. The mixture was poured into 250 ml of saturated KHCO$_3$ solution and extracted with CH$_2$Cl$_2$, the extract was dried over Na$_2$SO$_4$, the solvent was stripped off and the residue was recrystallized from acetone petroleum ether. 1.8 g of 6-[4-(3-N-formyl-N-methylamino-methylpyrrol-1-yl)-phenyl]-4, 5-dihydro-5-methylpyridazinone of melting point 148°–150° C. were obtained.

EXAMPLE 17

5 g (15 millimoles) of 6-[4-(3-N-formyl-N-methylaminomethylpyrrol-1-yl)-phenyl]-4, 5-dihydro-5-methylpyridazinone (Example 16) in 200 ml of methanol were stirred with 75 ml of 1 N NaOH for 3 days at 50° C. and the solvent was then stripped off, after which aqueous acetic acid was added and the mixture was extracted with ethyl acetate. The acid aqueous phase was rendered alkaline with 2 N NaOH and then extracted with ethyl acetate. This organic phase was dried over Na$_2$SO$_4$, the solvent was stripped off, one equivalent of tartaric acid in ethanol was added to the residue, the solvent was removed and the residue was recrystallized from dimethylformamide/ether. 5.4 g of 6-[-4-(3-N-methylaminomethylpyrrol-1-yl)-phenyl]-4,5-dihydro-5-methylpyridazinone of melting point 73°–75° C. were obtained.

EXAMPLE 18A 10 millimoles of 6-(4-aminophenyl)-4,5-dihydro-5-methylpyridazinone in toluene were refluxed with 13 millimoles of toluenesulfonic acid and 12 millimoles of 2,5-dimethoxy-3-dimethylaminomethyltetrahydrofuran with the addition of a little dimethylformamide, this procedure being carried out under a water separator. When the reaction was complete, which was determined by thin layer chromatography, the major part of the solvent was stripped off, the residue was taken up in dimethylformamide and the solution was poured into saturated NaHCO$_3$ solution. The aqueous phase was extracted with CH$_2$Cl$_2$ and the organic extract was dried over Na$_2$SO$_4$ and evaporated down in a rotary evaporator. The crude product was purified by column chromatography (SiO$_2$, CH$_2$Cl$_2$/CH$_3$OH). 6-[4-(3-Dimethylaminomethylpyrrol-1-yl)-phenyl]-4,5-dihydro-5-methylpyridazinone was obtained, this substance being identical to that synthesized in Example 3A.

The compounds of Examples 18B-K can be obtained in a manner similar to that described in Example 18A, by reacting the corresponding 6-(4-aminophenyl)-pyridazinones with 2,5-dimethoxy-3-dimethylaminomethyltetrahydrofuran or with 2,5-dimethoxy-3-piperidinomethyltetrahydrofuran.

| Example | $R^6$ | $R^1$ | $R^2$ | A | B | $R^4$ | $R^5$ |
|---|---|---|---|---|---|---|---|
| 18B | H | CH$_3$ | H | H | H | —(CH$_2$)$_5$— | |
| 18C | H | H | H | H | H | CH$_3$ | CH$_3$ |
| 18D | H | H | H | H | H | —(CH$_2$)$_5$— | |
| 18E | H | —CH$_2$— | H | H | CH$_3$ | CH$_3$ | |
| 18F | H | —CH$_2$— | H | H | —(CH$_2$)$_5$— | | |
| 18G | H | H | H | common bond | CH$_3$ | CH$_3$ | |
| 18H | H | H | H | common bond | —(CH$_2$)$_5$— | | |
| 18I | —(CH$_2$)$_2$— | H | H | H | CH$_3$ | CH$_3$ | |
| 18K | —(CH$_2$)$_2$— | H | H | H | —(CH$_2$)$_5$— | | |

EXAMPLE 19

Using a procedure similar to that described in Example 18A and reacting 1 g (5 millimoles) of 6-(4-aminophenyl)-4,5-dihydro-5-methylpyridazinone with 1.0 g (5 millimoles) of 2,5-dimethoxy-3-(N-formyl-N-methylaminomethyl)-tetrahydrofuran and 0.1 g (0.5 millimole) of toluenesulfonic acid in a mixture of 100 ml of toluene and 10 ml of DMF gave 6-[4-(3-N-formyl-N-methylaminomethylpyrrol-1-yl)-phenyl]-4,5-dihydro-5-methylpyridazinone, which was identical to the compound of Example 16.

EXAMPLE 20A

A solution of 3.24 g (10 millimoles) of 6-[4-(3-N-isopropylaminomethylpyrrol-1-yl)-phenyl]-4,5-dihydro-5-methylpyridazinone, 0.05 g (1 millimole) of sodium methylate and 10 g (167 millimoles) of methyl formate in 10 ml of dimethylformamide was stirred overnight at room temperature, poured into 100 ml of water and extracted with methylene chloride. The extract was dried over sodium sulfate, the solvent was stripped off, the residue was purified by column chromatography (silica gel, 4:1 CH$_2$Cl$_2$/CH$_3$OH), and the product was recrystallized from methanol. 1.25 g of 6-[4-(3-N-formyl-N-isopropylaminomethylpyrrol-1-yl)phenyl]-4,5-dihydro-5-methylpyridazinone of melting point 180°–181° C. were obtained.

$$R^3 = CH_2-\underset{\underset{\displaystyle R^4}{|}}{N}-CHO, \quad I$$

| Example | $R^6$ | $R^1$ | $R^2$ | A | B | $R^4$ |
|---|---|---|---|---|---|---|
| 20B | H | CH$_3$ | H | H | H | n-C$_6$H$_{13}$ |
| 20C | H | CH$_3$ | H | H | H | C$_6$H$_5$—CH$_2$— |
| 20D | H | CH$_3$ | H | H | H | C$_6$H$_5$—CH(CH$_3$)— |
| 20E | H | H | H | H | H | CH$_3$— |
| 20F | H | H | H | H | H | i-C$_3$H$_7$ |
| 20G | H | H | H | H | H | n-C$_6$H$_{13}$— |
| 20I | H | H | H | H | H | C$_6$H$_5$—CH$_2$— |
| 20K | H | —CH$_2$— | H | H | CH$_3$— | |
| 20L | H | —CH$_2$— | H | H | i-C$_3$H$_7$— | |
| 20M | H | —CH$_2$— | H | H | n-C$_6$H$_{13}$— | |
| 20N | H | —CH$_2$— | H | H | C$_6$H$_5$CH$_2$— | |
| 20O | H | —(CH$_2$)$_2$— | H | H | CH$_3$— | |
| 20P | H | —(CH$_2$)$_2$— | H | H | i-C$_3$H$_7$— | |
| 20Q | H | —(CH$_2$)$_2$— | H | H | n-C$_6$H$_{13}$— | |
| 20R | H | —(CH$_2$)$_2$— | H | H | C$_6$H$_5$—CH$_2$— | |
| 20S | H | H | CH$_3$ | H | H | CH$_3$— |
| 20T | H | H | CH$_3$ | H | H | i-C$_3$H$_7$— |
| 20U | H | H | CH$_3$ | H | H | n-C$_6$H$_{13}$— |
| 20V | H | H | CH$_3$ | H | H | C$_6$H$_5$CH$_2$— |
| 20W | H | H | CH$_3$ | common bond | CH$_3$— | |
| 20X | H | H | H | common bond | i-C$_3$H$_7$— | |
| 20Y | H | H | H | common bond | n-C$_6$H$_{13}$— | |

-continued $$R^3 = CH_2-\overset{R^4}{\underset{|}{N}}-CHO,\quad I$$

| Example | $R^6$ | $R^1$ | $R^2$ | A | B | $R^4$ |
|---|---|---|---|---|---|---|
| 20Z | H | H | H | common bond | | $C_6H_5CH_2-$ |
| 20AA | $-(CH_2)_2-$ | | H | H | H | $CH_3-$ |
| 20AB | $-(CH_2)_2-$ | | H | H | H | $i-C_3H_7-$ |
| 20AC | $-(CH_2)_2-$ | | H | H | H | $n-C_6H_{13}-$ |
| 20AD | $-(CH_2)_2-$ | | H | H | H | $C_6H_5CH_2-$ |

The compounds of Examples 20B–20AD were obtained similarly to Example 20, by reacting the compounds I in which $R^3$ is $CH_2NHR^4$ with methyl formate.

We claim:

1. A pyrrol-1-ylphenyldihydropyridazinone of the formula I

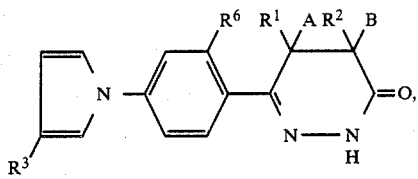

where $R^1$ is hydrogen, methyl or hydroxymethyl, $R^2$ is hydrogen or methyl or $R^1$ and $R^2$ together form a methylene or ethylene radical, A and B are each hydrogen, $R^3$ is formyl or hydroxymethyl or $CH_2-NR^4R^5$ where $R^4$ is $C_1-C_6$-alkyl or phenyl-$C_1-C_3$-alkylene and $R^5$ is hydrogen, $C_1-C_6$-alkyl or formyl or $R^4$ and $R^5$ together form a $C_4-C_7$-alkylene radical and $R^6$ is hydrogen, and its addition salts with acids.

2. A therapeutic composition which inhibits platelet aggregation, reduces blood pressure, inhibits gastric acid secretion and serves as a cardiotonic agent comprising a pharmaceutical excipient and an effective amount of a compound of claim 1 as the active compound.

3. The method of inhibiting platelet aggregation or gastric acid secretion or reducing blood pressure in a patient which comprises administering to the patient an effective amount of a compound of claim 1.

4. The compound of formula I, as set forth in claim 1, which is 6-[4-(3-dimethylanimomethyl-pyrrol-1-yl)-phenyl]-4, 5-dihydro-5-methylpyridazin-3-on.

5. The compound of formula I, as set forth in claim 1, which is 6-[4-(3-N-formyl-N-methylaminomethyl-pyrrol-1-yl)phenyl]-4, 5-dihydro-5-methylpyridazin-3-on.

6. The compound of formula I, as set forth in claim 1, which is 6-[4-(3-heptamethyleniminomethyl-pyrrol-1-yl)-phenyl]-4, 5-dihydro-5-methylpyridazin-3-on.

7. The compound of formula I, as set forth in claim 1, which is 6-[4-(3-N-benzylaminomethyl-pyrrol-1-yl)-phenyl]-4, 5-dihydro-5-methylpyridazin-3-on.

8. The compound of formula I, as set forth in claim 1, which is 6-[4-(3-N-benzyl-N-methylaminomethyl-pyrrol-1-yl)phenyl]-4,5-dihydro-5-methylpyridazin-3-on.

9. The compound of formula I, as set forth in claim 1, which is 6-[4-(3-N-benzyl-N-formylaminomethyl-pyrrol-1-yl)phenyl]-4,5-dihydro-5-methylpyridazin-3-on.

10. The compound of formula I, as set forth in claim 1, which is 6-[4-(3-formyl-pyrrol-1-yl)-phenyl]-4,5-dihydro-5-methylpyridazin-3-on.

11. The compound of formula I, as set forth in claim 1, which is 6-[4-(3-hydroxymethyl-pyrrol-1-yl)phenyl]-4,5-dihydro-5-methylpyridazin-3-on.

12. The compound of formula I, as set forth in claim 1, which is 6-[4-(3-hydroxymethyl-pyrrol-1-yl)phenyl]-4,5-dihydropyridazin-3-on.

13. The compound of formula I, as set forth in claim 1, which is 2-[4-(3-hydroxymethyl-pyrrol-1-yl)phenyl]-3,4-diazabicyclo[4.1.0]hepten-(2)-one-(5).

* * * * *